United States Patent [19]
Laske et al.

[11] Patent Number: 5,807,399
[45] Date of Patent: Sep. 15, 1998

[54] METHOD FOR REMOVAL OF CHRONICALLY IMPLANTED LEADS AND LEADS OPTIMIZED FOR USE THEREWITH

[75] Inventors: Timothy G. Laske, Shoreview; Pedro A. Meregotte, Coon Rapids; Michael R. Dollimer, Oakdale, all of Minn.

[73] Assignee: Medtronic, Inc., Minneapolis, Minn.

[21] Appl. No.: 736,000

[22] Filed: Oct. 23, 1996

[51] Int. Cl.$^6$ .................................................... A61N 1/05
[52] U.S. Cl. .......................................... 607/126; 606/108
[58] Field of Search .................................... 607/119, 122, 607/126–132; 600/374, 375; 606/1, 108

[56] References Cited

U.S. PATENT DOCUMENTS

| | | |
|---|---|---|
| 3,902,501 | 9/1975 | Citron et al. . |
| 4,437,475 | 3/1984 | White . |
| 4,506,679 | 3/1985 | Mann . |
| 4,506,680 | 3/1985 | Stokes . |
| 4,628,944 | 12/1986 | MacGregor et al. . |
| 5,231,996 | 8/1993 | Bardy et al. . |
| 5,383,924 | 1/1995 | Brehier .................................... 607/126 |
| 5,549,615 | 8/1996 | Hocherl et al. .......................... 606/108 |
| 5,632,749 | 5/1997 | Goode et al. ............................ 607/126 |

OTHER PUBLICATIONS

A.M. Bilgutay et al, "Incarceration of Transvenous Pacemaker Electrod. Removal by Traction", *American Heart Journal*, vol. 77, No. 3, pp. 370–379, Mar.,1969.

*Primary Examiner*—Jeffrey R. Jastrzab
*Attorney, Agent, or Firm*—Reed A. Duthler; Harold R. Patton

[57] ABSTRACT

A method of removing chronically implanted pacing leads and leads specifically adapted to be removed using the method. The leads are constructed so that upon tension applied to the electrode, it is withdrawn to a first location, so that upon further application of tension, the sheath located distal to the withdrawn electrode may collapse, enhancing its removability. In some embodiments of leads particularly adapted for use in conjunction with the method, the leads are provided with a mechanism for allowing breakage of the lead adjacent the points to which the electrode has been withdrawn, upon application of further tension to the electrode.

25 Claims, 7 Drawing Sheets

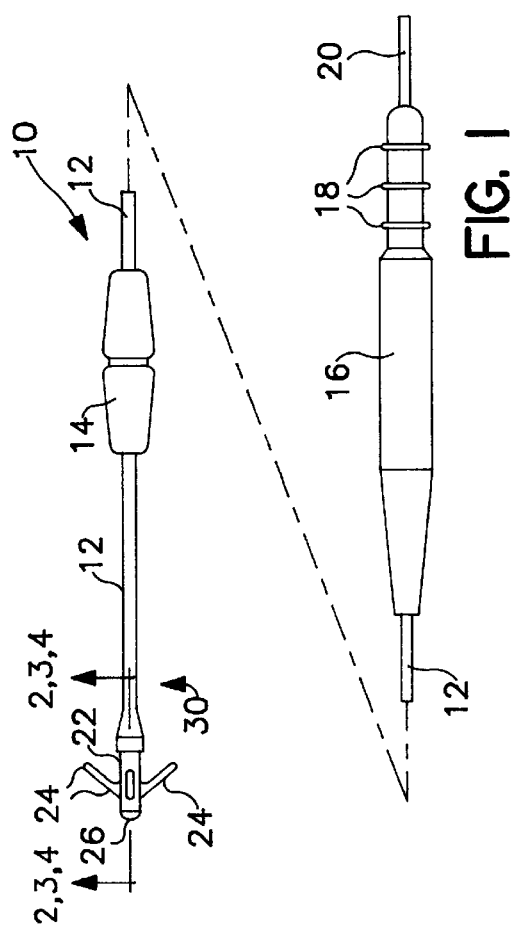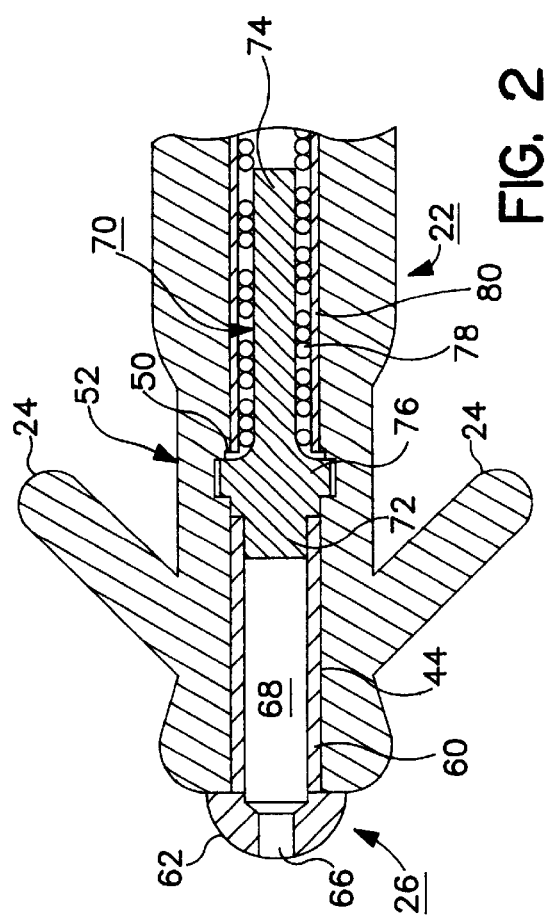

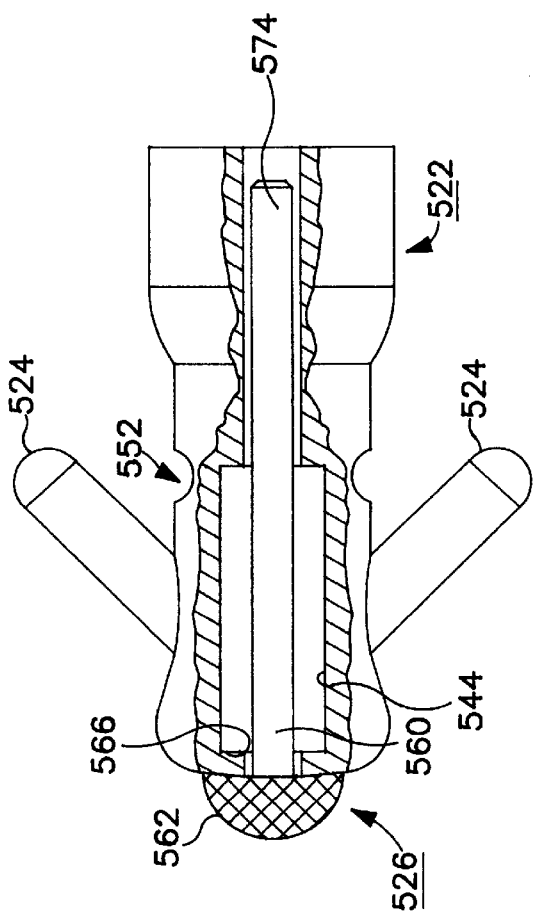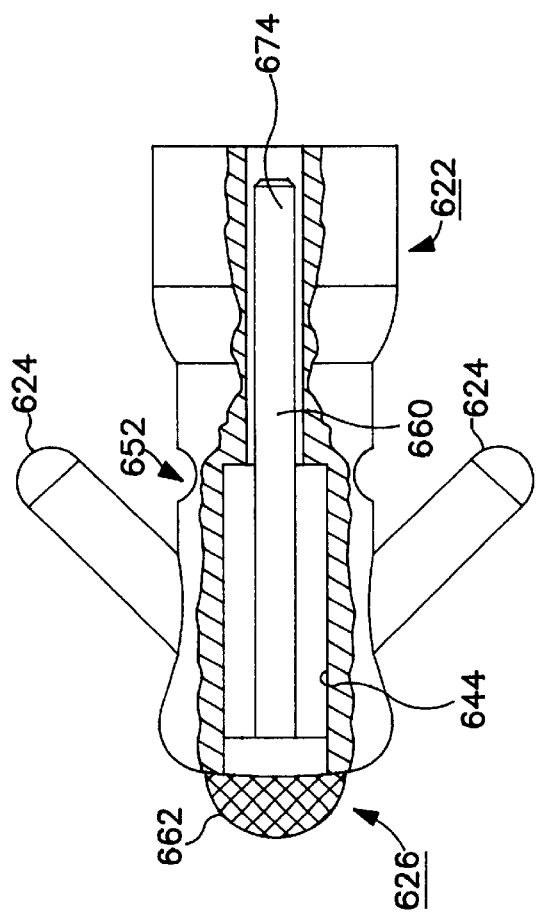

METHOD FOR REMOVAL OF CHRONICALLY IMPLANTED LEADS AND LEADS OPTIMIZED FOR USE THEREWITH

FIELD OF THE INVENTION

This invention relates to implantable medical leads, such as endocardial cardiac pacemaker and/or cardioverter/defibrillator leads, particularly such leads with passive fixation mechanisms at the distal end thereof which are encapsulated by tissue in-growth over a period of chronic implantation. More particularly, this invention relates to an improved structure for facilitating the removal of such leads by forceful traction after a period of chronic implantation.

BACKGROUND OF THE INVENTION

Various types of transvenous pacing and cardioversion/defibrillation leads have been developed for endocardial introduction into different chambers of a patient's heart and fixation at a selected site, typically the right ventricle apex or the right atrial appendage. These implantable leads usually are constructed having an outer biocompatible insulating sheath encasing one or more conductors, one of which is typically attached at its distal end to an exposed, tip electrode. In multipolar leads, additional conductors are provided in coaxial or co-linear relation to the first conductor and are connected at the distal end(s) thereof to electrode(s) or sensors situated along the lead body proximally to the distal tip electrode. The proximal ends of each conductor are coupled to a connector element which may include a single pin in unipolar leads and additional pins or in-line ring shaped connector elements in bipolar and multi-polar leads.

The tip electrode is usually placed in contact with endocardial tissue at the chosen site of the heart chamber by percutaneous introduction and passage through a venous access, often the sub-clavian vein or one of its tributaries, which leads to the heart chamber. The tip electrode generally is held in place actively by means of a member penetrating the endocardium or passively by engagement within spaces between trabeculae or against the endocardium. Passive fixation mechanisms typically include soft, pliant tines, or other projections which extend radially outward and usually at an acute angle extending proximally to urge the distal tip against the endocardium. Passive fixation mechanisms are typically formed as a molded, tubular fixation sheath with a plurality of tines projecting from the sheath in a certain pattern. The fixation sheath may be molded integrally with or sealed to the distal portion of the outer insulating sheath of the lead and extends proximally from to the exposed tip electrode. In leads provided with active fixation devices such as extendible helical members, the outer portion of the lead extending proximally from the exposed tip electrode also generally takes the form of a tubular sheath.

The fixation mechanism holds the tip electrode in position in the acute phase following implantation until the foreign body reaction leads to growth of tissue encasing the fixation mechanism in chronically implanted leads to fix the tip electrode in position in the heart and prevent its dislodgment during the life of the lead. In the acute phase, a blood clot forms about the fixation mechanism and insulating sheath (due to enzymes released as a result of irritation of the trabeculae tissue by the presence of the tip electrode) until scar tissue eventually forms, usually in three to six weeks. The acute fixation afforded by soft, pliant tines the most commonly used of the passive fixation approaches. However the active fixation, employing a retractable screw mechanism is preferred in certain patients and in certain sites in the heart where trabeculae are not present.

Although the state of the art in implanted pulse generator and endocardial lead technology has advanced considerably, endocardial leads nevertheless occasionally fail for a variety of reasons including insulation failure, failure of a sensor carried by certain leads, coiled wire conductor fracture, and an increase in lead/electrode resistance beyond a desirable level. Also, in some instances, it may be desirable to change the stimulation site in the heart, requiring the implantation of a further lead and positioning of its electrodes at the new site or relocation of the electrode of the existing lead.

There are a considerable number of patients who have had one or more, and sometimes as many as four or five previously and currently used leads left in place traversing their veins and with electrodes in their heart. The risks of leaving unusable leads in the heart and venous path include the following: an increased likelihood of infection; a potentially fatal complication which may necessitate removal of the lead; obstruction to blood flow, as in "SVC syndrome", and an increasing likelihood of the formation of blood clots which may embolize to the lung and produce severe complications and even death. In addition, extra leads in the heart can interfere with cardiac contraction and valve function, affecting cardiac output. Finally, the presence of unused leads in the venous pathway and inside the heart can cause considerable difficulty in the positioning and attachment of new endocardial leads in the desired sites.

Thus, it is desirable to remove old, unusable leads from the patient's body whenever possible. However, unless the lead fails and one of these problems manifests itself, surgeons usually have avoided attempts to remove previously implanted leads, because the risk of removing them otherwise exceeds the risk of leaving them in. The chronic encapsulation of the passive tine fixation mechanism works so very well that it is quite difficult to dislodge its distal end from the encapsulating tissue. The earliest removal techniques used in replacement surgery involved disconnecting the old lead connector from the pulse generator and then manually grasping and applying traction to the exposed proximal end of the lead and attempting to pull the lead out of the heart. If that failed, the patient was bedridden, and the proximal connector end was attached to a line and weight suspended by a pulley alongside the bed to allow the steady traction to gradually pull the encased distal tip electrode free from the patient's heart over several hours to days, as shown in FIG. 2 below and in commonly assigned U.S. Pat. No. 5,231,996 and described in published papers, such as "Incarceration of Transvenous Pacemaker Electrode. Removal By Traction." by A. M. Bilgutay et al., *American Heart Journal*, Vol. 77, No. 3, pp. 377–379, March 1969.

Grasping and applying traction on the proximal end of a chronically implanted lead results in directing pulling forces substantially along the length of the lead that are transmitted through the lead to its distal tip. Particularly in the case of tined leads, the fibrotic encapsulation enveloping the distal portion of the leads may provide substantial resistance to the pulling force, with the result that stress is placed on the lead as well as the heart. Endocardial tined lead construction typically includes a polymeric insulating outer sheath, within which one or more conductors are encased, separated by interior insulating sheathes or structure and attached to the distally located electrodes and proximally located connector elements. Such leads are of very small diameter, highly flexible, and strong enough to withstand stresses encountered in the body. Unfortunately, these characteristics, and the encapsulated tine fixation mechanism, tends to make their subsequent removal difficult. When the tine fixation mechanism is firmly encased and the lead is subjected to pulling forces along its length, it may disassemble. The polymeric outer insulating sheath can break away from the proximal and distal ends of the lead while the coiled wire conductor is stretched and straightened until it breaks or has to be cut off at the venous access site. The exposed end of a coiled wire conductor, once extended and stretched, may present the risk of cutting adjacent tissue if left in place. In such cases, only open heart surgery can fully remove the lead. A further complication of applying direct manual pulling force to the proximal end of the lead is the avulsion of the heart, which can induce arrhythmias or even lead to death. Thus, even if the lead is structurally capable of withstanding traction, at some point, the heart is not. Care must be taken to observe the procedure under fluoroscopy and to avoid either breaking the lead structure or causing avulsion of the heart.

To avoid the problems associated with traction applied to the proximal end of the lead body, some physicians cut the lead body and apply the weight or force to the conductor attached to the distal tip. The coiled wire conductor stretches considerably in the process, and may be virtually straightened before the applied force is transferred to the distal tip electrode. Alternatively, a locking stylet may be employed to apply traction to the distal end of the conductor, adjacent the electrode tip. The use of an internal longitudinal reinforcement or a non-elongating conductor coupled to the tip electrode have also been proposed. While these approaches have merit in transmitting the force, the force may still be insufficient to release the tines from the encapsulating sheath without subjecting the patient to one or more of the risks enumerated above. It is therefore still desirable to provide improved lead removal methods and lead designs which enhance the ease of removal of the lead after the fixation mechanism has been encapsulated in fibrous tissue and reduce the chance of adverse consequences associated with attempts to remove the lead.

SUMMARY OF THE INVENTION

It is therefore an object of the present invention to provide an improved method for removal of leads after encapsulation of the distal portion of the lead in fibrotic tissue. It is a further object of the present invention to provide an enhanced lead design, particularly optimized for use in conjunction with the improved method of lead removal.

The objects of the invention are accomplished in conduction with a two-step removal procedure, in which the first step comprises exerting traction on the tip electrode to move it proximally into the distal portion of the sheath. The second step comprises applying traction to the sheath either to result in inward collapse of the now empty distal portion of the sheath to ease its extraction from the fibrous sheath. In a preferred embodiment, the lead is also provided with means for allowing the distal portion of the sheath or to separate from the catheter, leaving it embedded in the fibrous sheath.

In conjunction with this removal methodology, various improvements may be made to the lead design. The distal portion of the lead body is constructed such that the electrode is movable proximally with the sheath to a first point in response to a traction force applied to the electrode, allowing the sheath to collapse inward and easing its retraction from the fibrotic tissue. In a preferred embodiment, the lead is also provided with means to allow separation of the distal portion of the sheath adjacent or distal to the first point, after retraction of the electrode, upon application of traction force to the sheath. Application of traction to the sheath after retraction of the electrode will thus either remove the distal portion of the sheath from the fibrotic tissue or will cause the distal portion of the sheath to detach, allowing it to remain in its fibrotic encapsulation.

In addition to or alternatively to the provision of a means for allowing separation of the distal end of the sheath, the lead may be configured such that when the electrode is retracted to the first point within the lead described above, it lodges at that point, requiring an increased traction force to move it further proximally within the lead body. As such, when the electrode is located at the first point, it can be used to apply traction only to that portion of the sheath distal to the electrode, as an alternative to applying traction to the proximal end of the sheath. If the lead is constructed to allow separation of the distal portion of the sheath, the traction force required to move the electrode proximal from the first point should be greater than the traction force required to separate the distal portion of the sheath, so that by applying traction only to the electrode, the distal portion of the sheath can either be removed from its fibrotic encapsulation or removed from the lead. The lead may also be provided with means for easing the retraction of the electrode into the sheath or, as an alternative to a means for allowing separation of the sheath, may be provided with reinforcing means for preventing detachment of the tines during removal of the sheath from its fibrotic encapsulation.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 1 is a side elevation view of a tined pacing lead of the general type to which the lead removal procedure of present invention may be applied;

FIG. 2 is an enlarged cross-section view of the distal portion of a lead to which the lead removal procedure of the present application may be applied.

FIGS. 10–13 are enlarged, partial cross-section views of the distal portions of leads adapted particularly for use with the lead removal procedure of the present invention by inclusion of mechanisms for assisting in the withdrawal of the electrode proximally into the sheath.

DETAILED DESCRIPTION OF THE PREFERRED EMBODIMENTS

Figure 3:
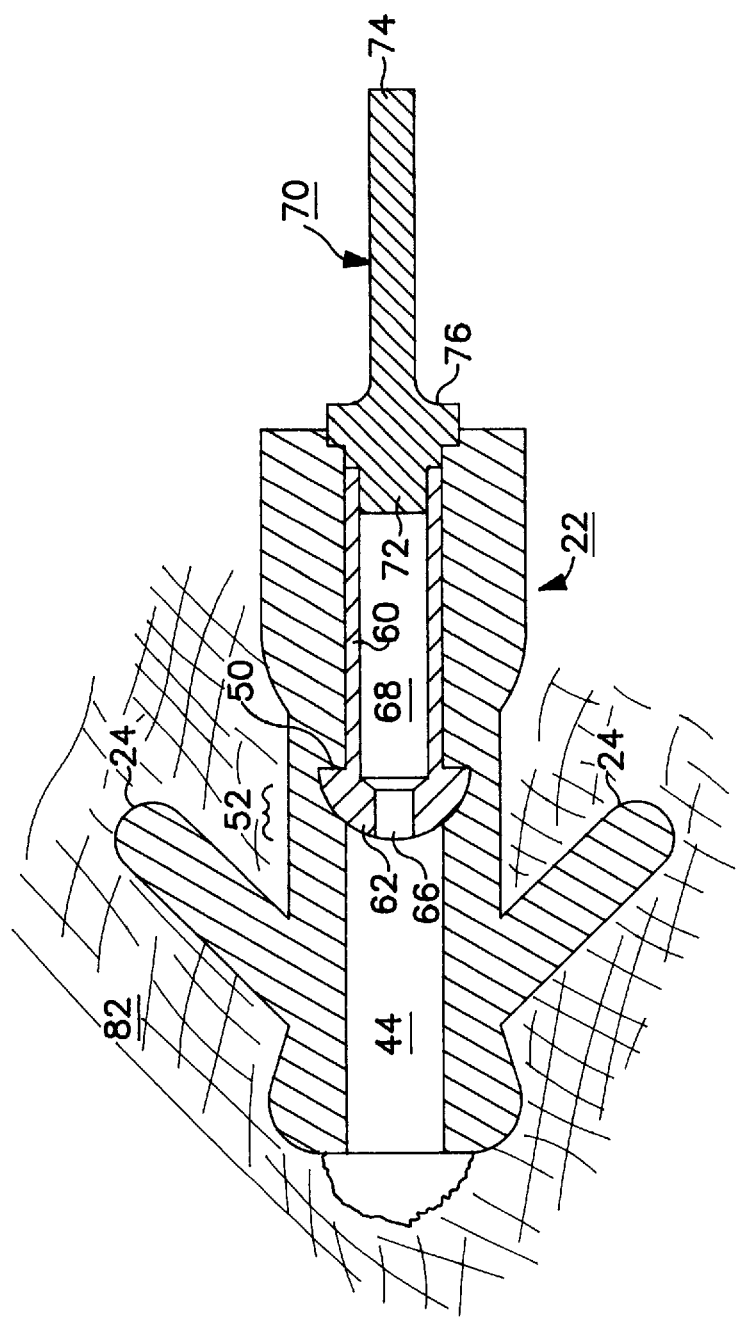
FIG. 3 is an enlarged cross-section view of the distal portion of the lead illustrated in FIG. 2, illustrating the first step of the lead removal procedure of the present invention, withdrawal of the electrode into the sheath by traction applied to the electrode.

FIG. 1 shows a side plan view of a simple, unipolar, endocardial pacing lead 10 of the type in which the present invention may be incorporated. The lead is provided with an elongated lead body which is covered with an insulation sheath 12, which may be fabricated of silicone rubber, polyurethane or other suitable plastic. A connector assembly 16, which is provided with sealing rings 18 and which carries connector element or pin 20 for engaging connector elements of an implantable pulse generator (not shown), is formed at the proximal end of lead body. Connector assembly 16 may be constructed using techniques known to the art, and may be fabricated of silicone rubber, polyurethane or other suitable plastic. Connector pin 20 may be fabricated of stainless steel or other conductive material.

At the distal end segment 30 of lead body 10 is tip electrode 26 and tine fixation mechanism 40 which is discussed in more detail below. The tine fixation mechanism 40 is immediately proximal to the exposed tip electrode 26 and includes tubular sheath 22 from which four tines 24 (three of which are visible) project out at an acute angle. Soft, pliant, tines 24 engage with heart tissue and urge tip electrode 26 into contact with the endocardium in a direction parallel to the lead axis. Soft, pliant, tines 24 are more fully described in commonly assigned U.S. Pat. No. 3,902,501, incorporated herein by reference. A fixation sleeve 14 is slideably mounted around lead body 10 and serves to stabilize the lead at the site of venous insertion as described in commonly assigned U.S. Pat. No. 4,437,475.

FIG. 2 illustrates the structure of the distal tip portion of the commercially available Medtronic Model 6932 lead, with which one embodiment of the removal procedure of the present invention may be practiced. The tip electrode 26 is shown exposed in a cross-section view of the surrounding tubular sheath 22 from which the tines 24 project. A cylindrical sheath lumen 44 extends axially through the sheath 22. Sheath 22 may be formed of medical grade silicone rubber or polyurethane and may be formed as a separate molded piece part or as part of the insulation sheath 12 (FIG. 1).

The distal tip electrode 26 comprises a semi-spherical, exposed electrode tip 62 and a cylindrical shank 60 extending proximally therefrom, located in but not adhesively attached to the interior suffice of the sheath lumen 44. The electrode tip 62 has an axial opening 66 formed therein to allow drug elution of anti-inflammatory drugs, for example, contained in a chamber 68 within cylindrical shank 60, into adjacent tissue to control the stimulation threshold in a manner well known in the art. The diameter of the electrode tip exceeds the diameter of the shank 60 and the diameter of sheath lumen 44. The shank 60 is attached at its proximal end to a coupling member 70 having a distal end 72 that is fitted into proximal end opening of the chamber 68 and closes it. The elongated proximal end 74 of coupling member 70 extends proximally within sheath lumen 44 and is attached to the distal end of the lead conductor 78 by means of crimp sleeve 80. Alternatively, a stranded or cabled conductor might be substituted for coiled conductor 78 to allow traction force to be placed on electrode 26 without requiring elongation of the conductor. For simplicity of illustration, the lead conductor and connection are not shown in later figures.

An enlarged diameter shoulder 76 is formed intermediate the distal and proximal ends 72 and 74 of coupling member 70. The shoulder 76 fits within an internal circumferential groove 50 formed in the sheath lumen 44, but is not adhered to it. The diameters of the internal groove 50 and the shoulder 76 exceed the diameters of the sheath lumen 44 and the elongated shank 60, and are less than the diameter of the electrode tip 62. The width of the annular groove 50 defines the length of a weaker section 52 of the sheath 22.

FIG. 3 illustrates the first step of applying the removal method of the present invention to the lead illustrated in FIG. 2, as well as to other similar existing leads. In the Model 6932, as depicted in FIG. 2 a relatively low magnitude retraction force, e.g. 1½ lb., may be applied to the tip electrode 26 by means of the conductor 78. If this force fails to exceed the force resisting removal of the sheath 22 from its fibrotic encapsulation 82, the electrode 62 and coupling member 70 will be retracted proximally into the sheath lumen 44 from the position shown in FIG. 2 into the position shown in FIG. 3, where the exposed electrode surface 62 is located in annular recess 50.

Figure 4:
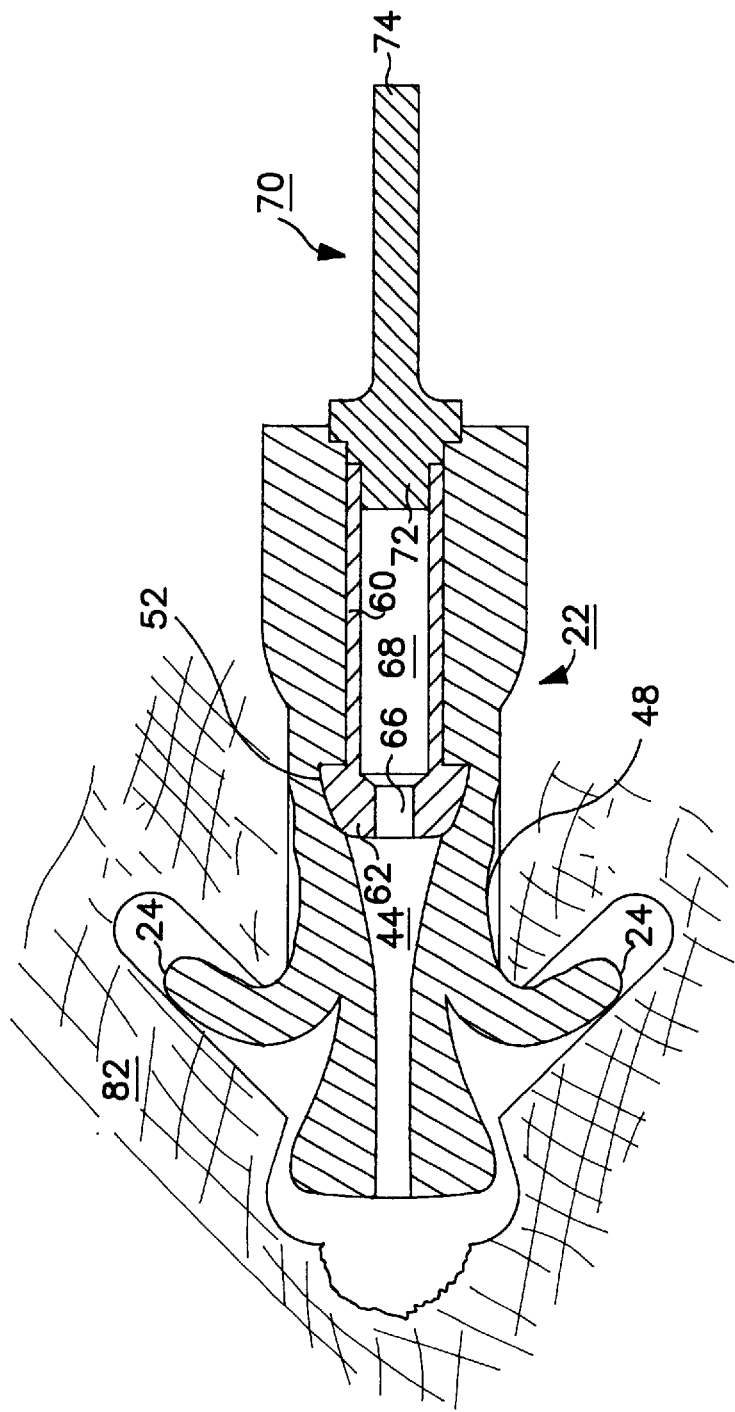
FIG. 4 is an enlarged cross-section view of the distal portion of the lead illustrated in FIG. 2, illustrating the second step of the lead removal procedure of the present invention, with the distal portion of the sheath collapsing, under traction applied to the sheath.

FIG. 4 illustrates the second step of applying the removal method of the present invention to the lead illustrated in FIG. 2. In FIG. 4, the distal portion of the lead is also depicted encapsulated in a mass of fibrous tissue 82, but traction force is now applied to the proximal end of the insulation sheath 12 (FIG. 1). The retraction of the shank 60 within the sheath lumen 44 allows the distal portion of the sheath 22 to collapse inward under tension and, in some cases, allow the sheath 22 and tines 24 to be removed from the fibrotic encapsulation.

Assuming that this operation is still not successful in releasing the sheath 22 from the fibrous tissue 82, the application of a substantially greater magnitude of retraction force, e.g. >4–5 lb., to the insulation sheath 12 will cause the sheath 22 to break, typically at weak section 52. The distal portion of sheath 22 and tines 24 are retained within the encapsulating fibrous tissue 82, and the foreign body reaction will continue to completely surround it and prevent it from ever being released to travel in the blood stream.

While the method of lead removal according to the present invention may be usefully practiced on the 6932 lead, and presumably on other similar leads, there are benefits to be gained by optimizing the structure of the lead to enhance the efficacy of the removal procedure. In the 6932 lead, while it would be possible to apply traction to the sheath 22 by continuing to exert traction on the lead conductor, the electrode will recede further proximally into the sheath 22, away from the desired point of separation of the sheath 22, with a traction force of substantially less (e.g. 2 lb.) than required to separate the distal portion of sheath 22. As a practical matter, this proximal progress will eventually be stopped because of the ring electrode present on the 6932 lead, (not illustrated in FIGS. 2–4), so that the conductor could theoretically be used to exert traction on the sheath 22 to either collapse the distal portion of sheath 22 or cause breakage of the sheath. However, such a mechanism would correspondingly not be available in a unipolar version of the lead, and may not be available in bipolar or multipolar leads differing in construction details from the 6932 lead. Further, it is believed desirable that if the conductor and electrode are to be used to exert traction on the sheath, this force should be applied adjacent to a desired point of breakage which is itself located adjacent and slightly proximal to the tines, so that the lead does not break at an undesired point or break remote from the distal tip, leaving a remaining lead segment which may be longer than desirable and/or which may be mechanically unstable. If the invention is practiced in leads employing active fixation devices,. it is desirable to locate the desired point of separation close to the distal end of the lead, preferrably within 2 cm, more preferrably within 1 cm, in order to minimize the length of the portion of the sheath left in the heart. To this end, modifications are proposed and illustrated in the Figures which follow which are believed to be applicable to most types of leads, and which are directed to optimizing the leads for removal.

Figure 5:
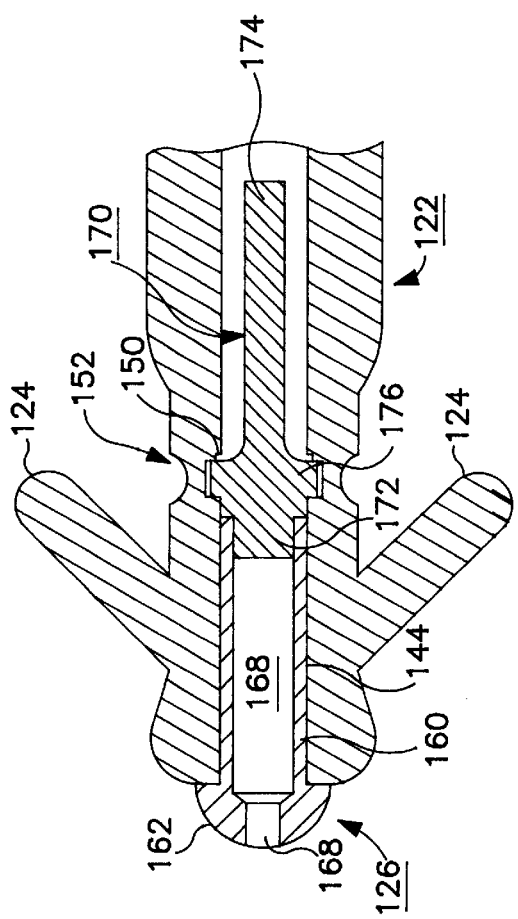
FIG. 5 is an enlarged cross-section view of a lead adapted particularly for use with the lead removal procedure of the present invention by inclusion of means for allowing separation of the distal portion of the sheath by applied retraction force.

FIG. 5 illustrates a cross-sectional view through the distal portion of a lead optimized for use with the lead removal procedure of the present invention. The lead is similar to that illustrated in FIG. 2, with the addition of an external groove 152 located radially outward of internal groove 150. Elements 122, 124, 144, 160, 162, 166, 168, 170, 172, 174 and 176 otherwise correspond to elements 22, 24, 44, 60, 62, 66, 68, 70, 72, 74 and 76 illustrated in FIG. 2. The addition of groove 152 defines a zone in which the sheath 122 may be readily separated, after the electrode 126 is withdrawn proximally into internal groove 150. Preferably, groove 152 is dimensioned such that when the proximal facing surface of electrode tip 162 is adjacent the distal facing surface of groove 150, the force necessary to separate the portion of the sheath 122 distal thereto is less than the force required to move the electrode tip 162 proximally out of internal groove 150. For example, further proximal retraction of the electrode 126 may require a traction force of 4 lb., while groove 150 may permit separation of the sheath 122 at a traction force of 2 lb. The forces required for proximal movement of the electrode 126 within sheath 122 may be adjusted by varying the depth of internal groove 150, the degree to which the electrode tip 162 extends radially outward of shank 160 and the relative dimensions of the sheath lumen 144 and shank 160. Dimensions will vary as a function of the materials employed and the over-all size of the lead, and will be determined empirically for each lead configuration. Preferably, the force required for further proximal movement of the electrode 126 will be required for further proximal movement of the electrode 126 is also greater than the force required for initial withdrawal of the electrode into the sheath 122. The point of initial retraction is preferrably located within 1–2 mm of the desired point of separation and both are both located closely proximal to and adjacent the tines, within 1 cm thereof, and preferrably within 1–2 mm.

Figure 6:
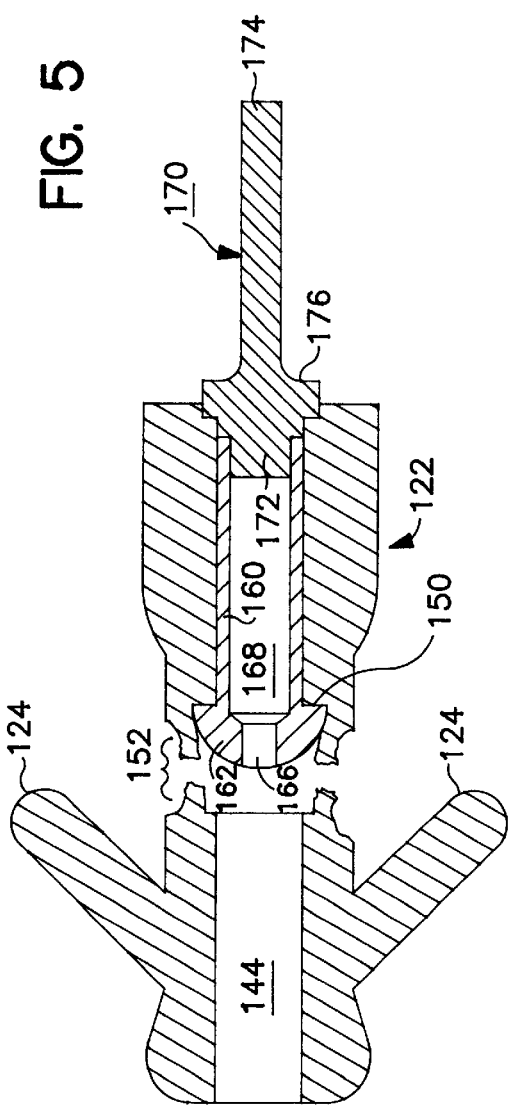
FIG. 6 is an enlarged cross-section view of the lead of FIG. 5, showing separation of the distal portion of the sheath.

FIG. 6 illustrates the lead of FIG. 5, with the electrode 126 retracted, after traction applied to the electrode 126 by the lead conductor (not illustrated) has caused separation of the distal portion of the sheath. By configuring the lead as described above, the traction force applied to the sheath 122 is applied at the point at which the proximally facing surface of the electrode tip 162 engages the distally facing surface of internal groove 150. The force applied is thus limited to the distal portion of the sheath, rather than being applied over an extended length of the sheath. Inward contraction of the portion of the sheath 122 is thereby localized to the distal portion of the sheath which carries the tines, and force tending to separate the distal portion of the sheath is applied adjacent the desired separation point. Both of these factors are believed to assist in assuring that if the sheath 122 can be removed intact, it will be, and that if the sheath does separate, it does so precisely as desired, leaving a only a short, readily encapsulated segment behind.

Figure 8:
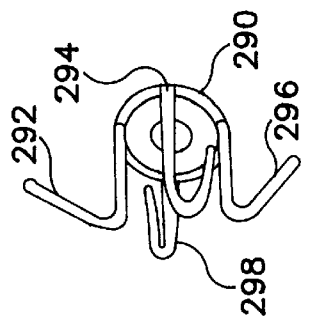
FIG. 8 is a perspective view of the reinforcement mechanism of the lead illustrated in FIG. 7.
Figure 7:
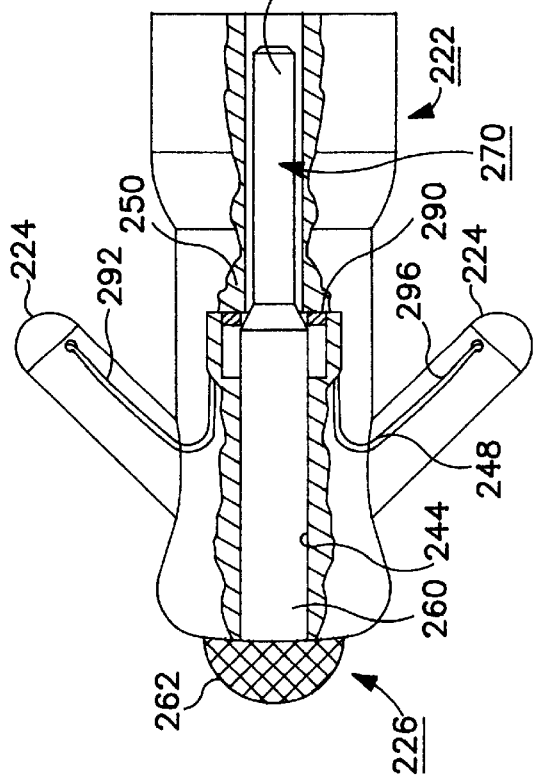
FIG. 7 is an enlarged, partial cross-section view of the distal portion of a lead adapted particularly for use with the lead removal procedure of the present invention by inclusion of a mechanism for reinforcing the tines.
Figure 9:
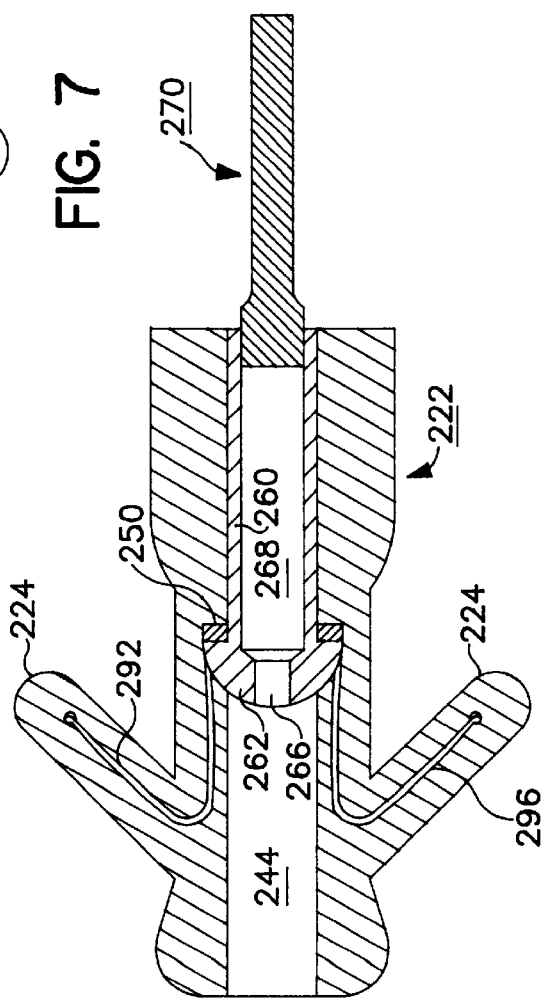
FIG. 9 is an enlarged cross-section view of the distal segment of the lead illustrated in FIG. 7 with the tip electrode retracted.

Turning to FIGS. 7–9, a further embodiment of the invention is depicted whereby the tines 224 are strengthened, and retraction force is conveyed down the length of the tines 24 when the electrode 226 is withdrawn proximally into sheath lumen 244. The proximal portion of internal groove 250 carries a reinforcing ring 290 having reinforcing filaments 292, 294, 296, 298 that each are attached to the ring and extended into one the tines 224. The filaments 292, 294, 296, 298 and the ring 290 may be formed of a material, e.g. polytetrafluoroethylene, having a higher tensile strength than the material used to mold the sheath 222. When traction force is applied to electrode 226, the shank 260 passes through ring 290 and the proximally facing surface of electrode tip 262 comes to rest against the distally facing surface of ring 290. Subsequent traction force applied to the electrode 260 is thereby also applied to the tines 224.

The ring 290 and associated filaments 292, 294, 296, and 298 are shown in perspective view in FIG. 8. The lead is shown in cross section with the electrode 226 retracted in FIG. 9. In this view the relationship of electrode shank 260 and coupling member 270 is also visible.

In the embodiment illustrated in FIGS. 7–9, while the retraction in the manner of FIG. 4 is possible, it is not possible to separate the distal section of sheath 222 without applying excessive force to the heart. However, greater retraction force can be applied to effect removal of the entire sheath 222 without risk of detachment of the tines 224.

FIGS. 10–13 depict various embodiments of leads optimized for use with the lead removal procedure of the present invention. The leads are similar to that illustrated in FIGS. 5 and 6, with the addition of means for minimizing the traction force necessary to initially withdraw the tip electrode into the sheath. Although not specifically shown, it will be understood that these features of the leads of FIGS. 10–13 may also be incorporated in leads employing the reinforcement mechanism of the lead illustrated in FIGS. 7–9.

Figure 10:
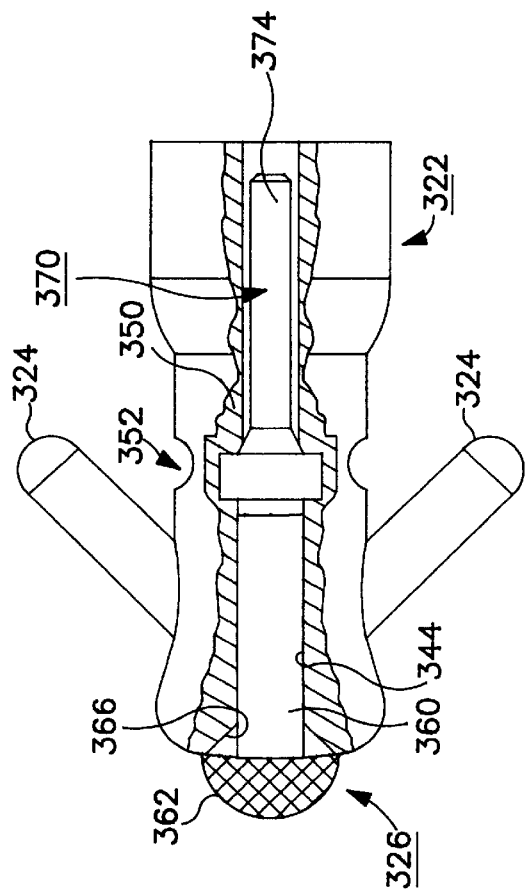

In FIG. 10 an internal chamfer 366 is provided at the distal end of the sheath lumen 344 to ease the entry of electrode 326 into the lumen. Elements 322, 326, 324, 350, 352, 360, 362, 370 and 374 all otherwise correspond to elements 122, 126, 124, 150, 152, 160, 162, 170 and 174 of FIG. 5.

Figure 11:
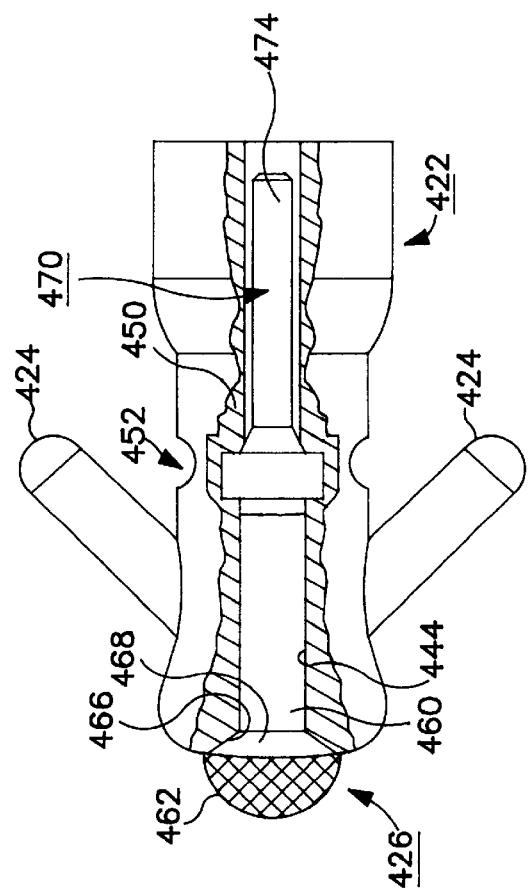

In FIG. 11 an internal chamfer 466 is provided at the distal end of the sheath lumen 444 as well as a corresponding taper 468 on the proximal surface of electrode tip 462, to further ease the entry of electrode 426 into the lumen. Elements 422, 426, 424, 450, 452, 460, 462, 470 and 474 all otherwise correspond to elements 122, 126, 124, 150, 152, 160, 162, 170 and 174 of FIG. 5.

In FIG. 12, a reduced diameter electrode shank 560 is provided, the proximal end 574 of which is employed to couple the electrode 526 to the lead conductor (not illustrated). The distal portion of the sheath lumen 544 in sheath 522 is enlarged so that it is approximately equal to the outer diameter of electrode tip 562. The shank 560 extends through an orifice 566 of a diameter less than the outer diameter of the electrode tip 562, preventing inadvertent proximal movement of the electrode 526. Once the electrode tip 626 is pull into the sheath lumen 544, it may readily be retracted until the proximally facing surface of the electrode tip 562 is located against the distally facing surface of the enlarged distal portion of sheath lumen 544. Traction applied to electrode 526 thereafter may be employed to withdraw or separate the portion of sheath 522 distal to groove 522. Elements 522, 526, 524, 552, 660, 562, and 574 all otherwise correspond functionally to elements 122, 126, 124, 152, 160, 162, and 174 of FIG. 5.

Finally, in FIG. 13, a variation is shown employing an electrode 626 having its electrode tip 662 contained in part within an enlarged distal portion of sheath lumen 644. All of the above-described embodiments rely at least in part on the distal opening of the sheath lumen being smaller than the diameter of the electrode tip to prevent inadvertent retraction of the electrode. In the embodiment of FIG. 13, however, the frictional interference between the outer circumferential surface of electrode tip 662 and the inner surface of lumen 644 is the primary means for preventing inadvertent proximal movement of electrode 626. In this embodiment, traction applied to electrode 626 results in proximal movement of electrode 626 until the proximally facing surface of the electrode tip 662 is located against the distally facing surface of the enlarged distal portion of sheath lumen 644. Traction applied to electrode 626 thereafter may be employed to withdraw or separate the portion of sheath 622 distal to groove 622. Elements 622, 626, 624, 652, 660, 662, and 674 all otherwise correspond functionally to elements 122, 126, 124, 152, 160, 162, and 174 of FIG. 5. In this embodiment, electrode 626 can be retracted proximally into sheath 622 without the necessity of substantially distorting sheath 622.

In practice, leads optimized for use according to the present invention may also incorporate filaments according to the above-referenced '996 patent to minimize the stretching of a coiled wire conductor, if employed. In this regard, filament(s) preferably take the form of Dacron polyester woven yarn or cord having a size of approximately 2,600 denier that is mechanically attached to the proximal connector and the distal electrode shank by passing the ends of the filament through holes therein and tying the ends off, the yarn either wound loosely about a coiled wire conductor or extended through the lumen of the coiled wire conductor.

The present invention may also be used in leads of the type described that have inextensible conductors such as substantially straight wire, stranded or cabled lead conductors, which would allow retraction of the electrode without the necessity of first straightening the conductor. The method of the present invention may alternatively be practiced using locking stylets or similar tools to apply traction to the electrode, although this does add complexity to the removal procedure.

It should also be understood that while the means for defining the retraction force necessary to retract the electrodes proximally beyond the vicinity of the desired point of initial retraction are described above as internal surfaces formed as part of the internal lumen of the sheath which interact with expanded portions of the electrode tips, other mechanisms for controlling the required retraction forces, such as other types of mechanical interlock and/or frictional interference may be substituted within the scope of the invention. In addition, while the greatest benefit of the invention is believed to be realized in conjunction with tined leads, the invention is also useful in the context of other types of passive fixation mechanisms, such as fins, loops or other flexible extensions from the sheath. Although of lesser benefit in the context of active fixation systems such as penetrating barbs, screws, and so forth, the invention is also believed useful in such contexts to the extent that fibrous tissue adherence to the distal portion of the lead sheath remains a problem.

While there has been shown what are considered to be preferred embodiments of the invention, it will be manifest that the various improvements and features may be combined in different combinations than specifically illustrated. It is intended, therefore, that the specific embodiments described above should be considered exemplary, rather than limiting with regard to the following claims.

In conjunction with the above specification, we claim:

1. A method of removing a fibrotically encapsulated chronically implanted endocardial cardiac lead of the type having an elongated insulating sheath having an internal lumen, an electrode extending from a distal end of the sheath, and a conductor coupled to the electrode, extending within the sheath, comprising:

applying traction to the electrode to retract the electrode proximally to a first position within the sheath; and while the electrode is located at the first position, applying traction to the sheath to collapse the sheath distal to the electrode and remove it from encapsulating fibrotic tissue.

2. A method of removing a fibrotically encapsulated chronically implanted endocardial cardiac lead of the type having an elongated insulating sheath having an internal lumen, an electrode extending from a distal end of the sheath, and a conductor coupled to the electrode, extending within the sheath, comprising:

applying traction to the electrode to retract the electrode proximally to a first position within the sheath; and while the electrode is located at the first position, applying traction to the sheath to separate the sheath distal to the electrode from the lead, allowing removal of the rest of the lead.

3. A method according to claim 1 or claim 2 wherein the step of applying traction to the electrode comprises applying traction to the conductor.

4. A method according to claim 1 or claim 2 wherein the step of applying traction to the sheath comprises applying traction to the conductor.

5. A method of removing a fibrotically encapsulated chronically implanted endocardial cardiac lead of the type having an elongated insulating sheath having an internal lumen and means for accomplishing passive fixation of the lead extending from the sheath adjacent its distal end, an electrode extending from the distal end of the sheath, and a conductor coupled to the electrode, extending within the sheath, comprising:

applying traction to the electrode to retract the electrode proximally to a first position within the sheath proximal to the fixation means; and while the electrode is located at the first position, applying traction only to a portion of the sheath distal to the electrode to collapse the sheath distal to the electrode and remove it from encapsulating fibrotic tissue.

6. A method of removing a fibrotically encapsulated chronically implanted endocardial cardiac lead of the type having an elongated insulating sheath having an internal lumen and means for accomplishing passive fixation of the lead extending from the sheath adjacent its distal end, an electrode extending from the distal end of the sheath, and a conductor coupled to the electrode, extending within the sheath, comprising:

applying traction to the electrode to retract the electrode proximally to a first position within the sheath; and while the electrode is located at the first position, applying traction only to a portion of the sheath distal to the electrode to separate the sheath distal to the electrode from the lead, allowing removal of the rest of the lead.

7. A method according to claim 5 or claim 6 wherein the step of applying traction to the electrode comprises applying traction to the conductor.

8. A method according to claim 5 or claim 6 wherein the step of applying traction to the sheath comprises applying traction to the conductor.

9. A method according to claim 5 or claim 6 wherein the step of applying traction to the sheath comprises applying traction only to a portion of the sheath extending 1 cm or less proximally from the fixation means.

10. An implantable lead, comprising:

an elongated insulating sheath having an internal lumen;

an electrode extending from a distal end of the sheath;

an elongated conductor extending along the sheath and coupled to the electrode;

means for allowing separation of the sheath at a first location in response to traction force of a first magnitude applied to the sheath;

means for allowing the electrode to retract into the sheath to a second location adjacent the first location, in response to a traction force applied to the electrode;

means for preventing retraction of said electrode into said sheath proximal to said second location in response to a traction force less than a second magnitude greater than said first magnitude.

11. A lead according to claim 10, wherein the sheath is provided with passive fixation members extending from the sheath and wherein the first and second locations are both located proximal to the passive fixation members.

12. A lead according to claim 11 wherein the first and second locations are within 1 cm of the fixation members.

13. An implantable lead, comprising:

an elongated insulating sheath having an internal lumen open to a distal end of the sheath, a weakened zone allowing separation of the sheath in response to a traction force of a first magnitude and enclosing a distally facing internal surface adjacent the weakened zone;

an electrode extending from a distal end of the sheath, having a proximally facing surface and retractable proximally into the lumen of the sheath until the proximally facing surface of the electrode contacts the distally facing internal surface within the sheath, and not further retractable in response to traction force less than a second magnitude greater than the first magnitude; and an elongated conductor extending along the sheath and coupled to the electrode.

14. A lead according to claim 13, wherein the sheath is provided with passive fixation members extending from the sheath and wherein the weakened zone and distally facing internal surface are both located proximal to the passive fixation members.

15. A lead according to claim 13 wherein the weakened zone and distally facing internal surface are within 1 cm of the fixation members.

16. A lead according to claim 10 or claim 13 further comprising means for easing retraction of said electrode into said sheath.

17. A lead according to claim 16 wherein said easing means comprises a chamfered surface at the distal end of the internal lumen of the sheath.

18. A lead according to claim 16 wherein said easing means comprises a beveled, proximally facing surface of the electrode.

19. A lead according to claim 16 wherein said easing means comprises an increased diameter portion of the internal lumen of the sheath.

20. A lead according to claim 19 wherein said increased diameter portion of the lumen extends to the distal end of the sheath.

21. A lead according to claim 10 or claim 13, further comprising means for preventing inadvertent retraction of the electrode into the internal lumen of the sheath.

22. An implantable lead, comprising:

an elongated insulating sheath having an internal lumen and having fixation members extending therefrom;

an electrode extending from a distal end of the sheath and retractable into the sheath to a first location proximal to the fixation members, in response to traction applied to the electrode;

an elongated conductor extending along the sheath and coupled to the electrode; and reinforcements extending from the first location, coupled to the fixation members.

23. A lead according to claim 22 further comprising means for preventing retraction of the electrode beyond the first point, coupled to the reinforcements.

24. A lead according to claim 22 or 23 wherein the reinforcements are filaments.

25. A lead according to claim 24 wherein the preventing means is a ring, through which the conductor passes.

* * * * *